US00PP14654P29

(12) United States Plant Patent
van Gaalen

(10) Patent No.: US PP14,654 P2
(45) Date of Patent: Mar. 30, 2004

(54) PHLOX PLANT NAMED 'FANCY FEELINGS'

(50) Latin Name: *Phlox paniculata*
Varietal Denomination: Fancy Feelings

(75) Inventor: Irenaeus Antonius Maria van Gaalen, Rijswijk (NL)

(73) Assignee: R. Van Gaalen B.V., Rijswijk (NL)

( * ) Notice: Subject to any disclaimer, the term of this patent is extended or adjusted under 35 U.S.C. 154(b) by 0 days.

(21) Appl. No.: 10/377,498

(22) Filed: Feb. 28, 2003

(51) Int. Cl.[7] ..... A01H 5/00
(52) U.S. Cl. ..... Plt./320
(58) Field of Search ..... Plt./320

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Phlox plant named 'Fancy Feelings', characterized by its upright plant habit; dark green leaves; and panicles of numerous white and dark pink bi-colored flowers.

2 Drawing Sheets

Botanical classification/cultivar designation: *Phlox paniculata* cultivar Fancy Feelings.

BACKGROUND OF THE INVENTION

The present Invention relates to a new and distinct cultivar of Phlox plant, botanically known as *Phlox paniculata*, and hereinafter referred to by the name 'Fancy Feelings'.

The new Phlox is a naturally-occurring whole plant mutation of the *Phlox paniculata* cultivar Bright Eye Elite, not patented. The new Phlox was discovered by the Inventor in a controlled environment in Rijswijk, The Netherlands, within a population of plants of 'Bright Eye Elite' in September, 2001.

Asexual reproduction of the new cultivar by vegetative cuttings taken at Rijswijk, The Netherlands since December, 2001, has shown that the unique features of this new Phlox are stable and reproduced true to type in successive generations.

SUMMARY OF THE INVENTION

Plants of the cultivar Fancy Feelings have not been observed under all possible environmental conditions. The phenotype may vary somewhat with variations in environment such as temperature and light intensity without, however, any variance in genotype.

The following traits have been repeatedly observed and are determined to be the unique characteristics of 'Fancy Feelings'. These characteristics in combination distinguish 'Fancy Feelings', as a new and distinct cultivar:

1. Plants of the new Phlox have an upright plant habit.
2. Plants of the new Phlox have dark green leaves.
3. Plants of the new Phlox are freely flowering.
4. Inflorescences of plants of the new Phlox have numerous dark pink and white bi-colored flowers.

Plants of the new Phlox are most similar to plants of the parent plant, the cultivar Bright Eye Elite. In side-by-side comparisons conducted in Rijswijk, The Netherlands, plants of the new Phlox differed from plants of the cultivar Bright Eye Elite in the following characteristics:

1. Plants of the new Phlox had smaller flowers than plants of the cultivar Bright Eye Elite.

2. Plants of the new Phlox had smaller and narrower petals than plants of the cultivar Bright Eye Elite.
3. Plants of the new Phlox and the cultivar Bright Eye Elite differed in petal coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Phlox.

The photograph on the first sheet comprises a side perspective view of a typical flowering plant of 'Fancy Feelings'.

The photograph on the second sheet comprises a close-up view of typical flowers of 'Fancy Feelings'.

DETAILED BOTANICAL DESCRIPTION

The following observations, measurements and values describe plants of the new cultivar grown in a glass-covered greenhouse during the summer in Den Hoorn, The Netherlands. Plants used in the photographs and the detailed botanical description were about 2 years from planting rooted cuttings. During the production of the plants, day temperatures ranged from 18 to 32° C. and night temperatures ranged from 10 to 18° C. Color references are made to The Royal Horticultural Society Colour Chart, 1995 Edition, except where general terms of ordinary dictionary significance are used.

Botanical classification: *Phlox paniculata* cultivar Fancy Feelings.

Parentage: Naturally-occurring whole plant mutation of *Phlox paniculata* cultivar Bright Eye Elite, not patented.

Propagation:

*Type cutting.*—Vegetative cuttings.

*Time to produce a rooted cutting.*—Summer: About 20 days at 20° C. Winter: About 35 days at 12° C.

*Root description.*—Thick, fibrous.

Plant description:

*Form.*—Upright, conical to narrowly inverted triangle.

*Usage.*—Perennial garden plant; cut flower.

*Crop time.*—From cuttings, about 25 weeks are required to produce fully-grown flowering plants in 1.5-liter containers.

*Plant height.*—About 75 cm.

*Area of spread.*—About 50 cm.

*Vigor.*—Moderately vigorous.

*Branching habit.*—Freely basal branching; about seven stems develop per plant during the flowering season.

*Stems.*—Length: About 75 cm. Diameter: About 6 mm. Internode length: About 4.8 cm. Texture: Smooth, glabrous. Strength: Strong. Color: 143B to 143C.

*Foliage description.*—Leaves simple, opposite, generally symmetrical, durable and long persisting. Length: About 14.4 cm. Width: About 4.3 cm. Shape: Elliptic to narrowly elliptic. Apex: Acute. Base: Attenuate. Margin: Serrulate. Texture, upper and lower surfaces: Somewhat leathery; glabrous. Venation pattern: Pinnate. Color: Young foliage, upper surface: 143A; margins, much darker than 143A. Young foliage, lower surface: 137C; margins, more green than 200C. Mature foliage, upper surface: 137A. Mature foliage, lower surface: 137C. Venation, upper surface: 138B. Venation, lower surface: 143C. Petiole: Length: About 3 mm. Diameter: About 3 mm. Texture, upper and lower surfaces: Smooth, glabrous. Color, both surfaces: 143C.

Flower description:

*Flower type and habit.*—Single salverform flowers arranged on compound terminal panicles.

*Natural flowering season.*—Flowering continuous during the summer from July to August in Den Hoorn, The Netherlands.

*Quantity.*—Freely flowering with about 600 flowers per flowering stem over the entire flowering period.

*Fragrance.*—Not detected.

*Flower longevity.*—About 14 days on the plant.

*Flower buds.*—Length: About 1.1 cm. Diameter: About 4 mm. Shape: Oblong. Color: 186A.

*Inflorescence length.*—About 25 cm.

*Inflorescence diameter.*—About 22 cm.

*Flower length.*—About 2.4 cm.

*Flower diameter.*—About 2 cm.

*Petals.*—Quantity/arrangement: Five petals fused at base. Length: About 2.5 cm. Diameter: About 4 mm. Shape: Narrowly oblong. Apex: Aristate. Margin: Entire. Texture, upper and lower surfaces: Smooth, glabrous. Color: When opening and fully opened, upper surface: Close to 155D irregularly overlain with 61B to 61C. When opening and fully opened, lower surface: Close to 155D irregularly overlain with 61A to 71B.

*Sepals.*—Quantity/arrangement: Five sepals fused at base. Length: About 9 mm. Diameter: About 1 mm. Calyx shape: Campanulate. Apex: Narrowly apiculate. Margin: Entire. Texture, upper and lower surfaces: Smooth, glabrous. Color: Immature and mature, upper surface: 137C. Immature and mature, lower surface: 200B; towards the base, 143C.

*Peduncles.*—Angle: Upright to about 30 to 40° from vertical. Strength: Strong. Length: About 20 mm. Diameter: About 3.5 mm. Color: 143B to 143C.

*Pedicels.*—Angle: Upright to about 40° from stem. Strength: Strong. Length: About 4 mm. Diameter: About 1 mm. Color: 143B.

*Reproductive structures.*—Androecium: Stamen quantity: About four per plant. Ather length: About 3 mm. Anther shape: Oblong. Anther color: 157D. Pollen amount: Scarce. Gynoecium: Pistil quantity: One per flower. Pistil length: About 8 mm. Stigma shape: Cleft; three-parted. Stigma color: 157B. Style length: About 7 mm. Style color: 157B. Ovary color: 141B to 141C.

Disease/pest resistance: Resistance to pathogens or pests common to phlox has not been observed.

It is claimed:

1. A new and distinct cultivar of Phlox plant named 'Fancy Feelings', as illustrated and described.

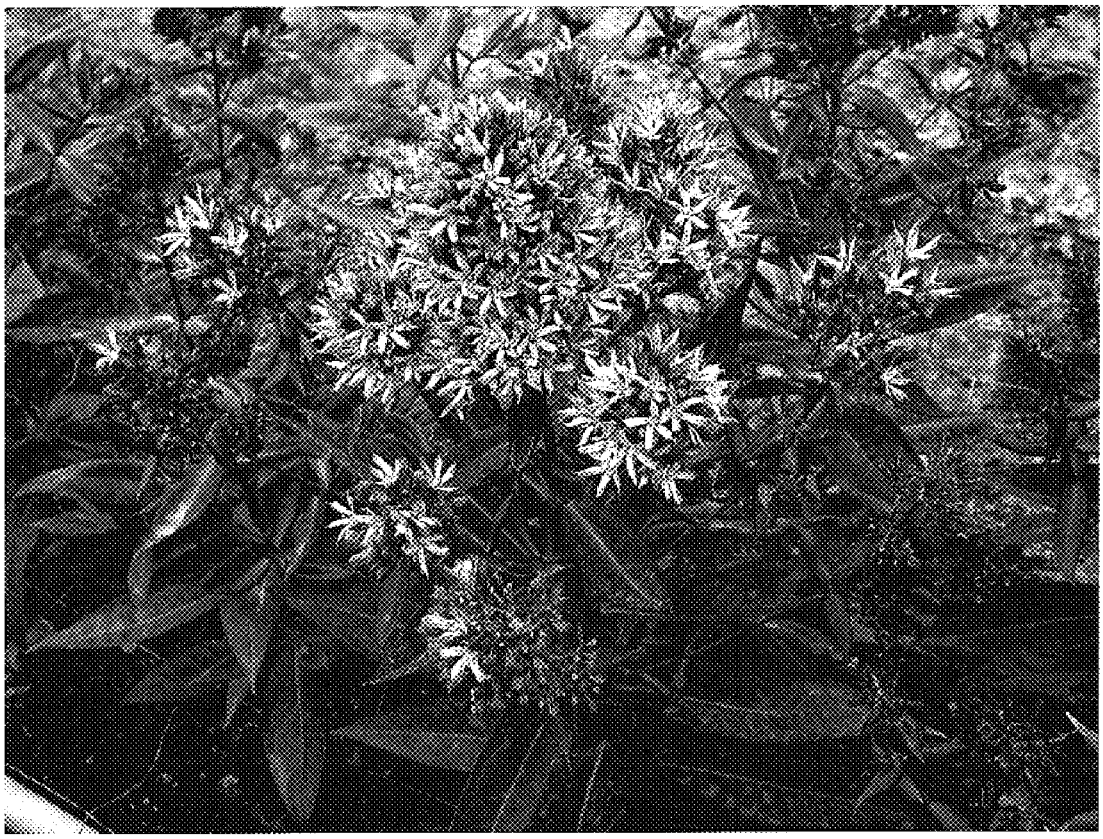

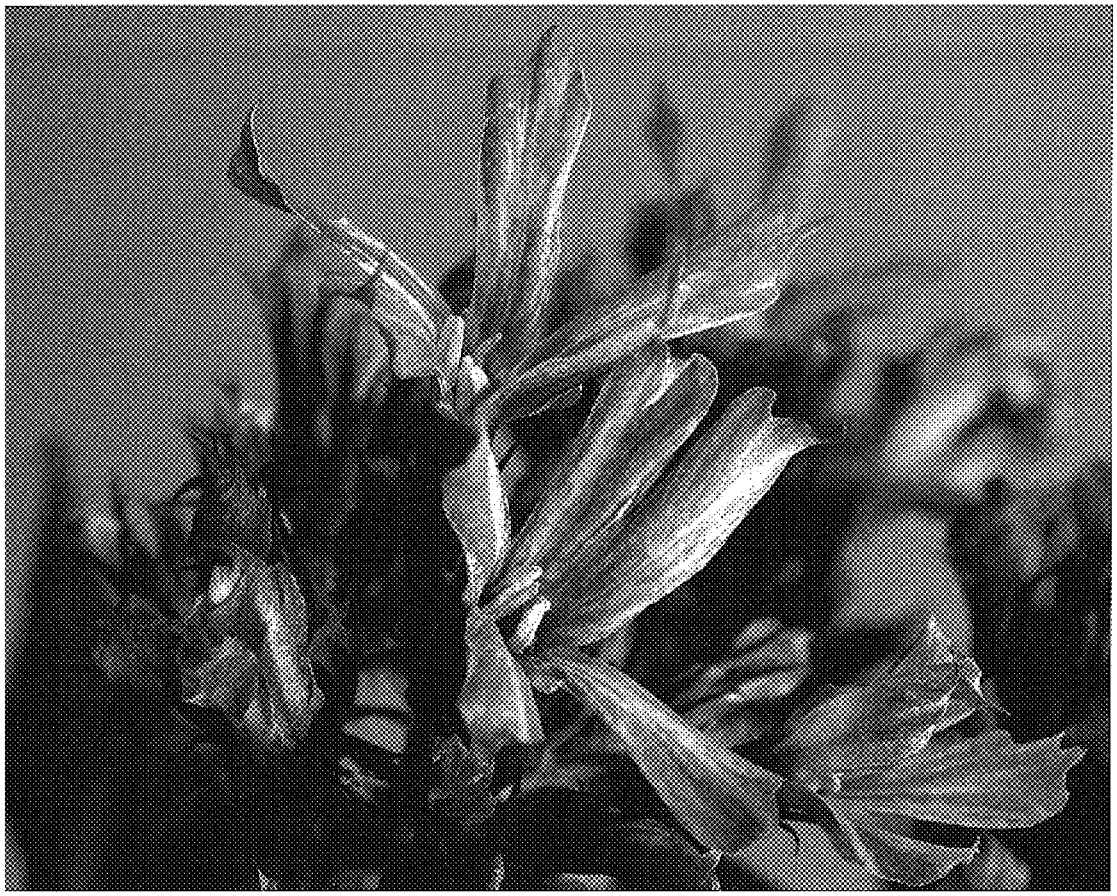

* * * * *